(12) United States Patent
Helland et al.

(10) Patent No.: US 6,687,549 B1
(45) Date of Patent: Feb. 3, 2004

(54) LEAD CONDUCTOR LUMEN WITH CROSS-SECTIONAL SHAPE TO MINIMIZE EFFECTS OF COMPRESSIVE FORCES

(75) Inventors: John R. Helland, Saugus, CA (US); Kevin L. Morgan, Simi Valley, CA (US); Phong D. Doan, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 217 days.

(21) Appl. No.: 09/911,978

(22) Filed: Jul. 25, 2001

(51) Int. Cl.[7] .................................................. A61N 1/06
(52) U.S. Cl. ....................................................... 607/122
(58) Field of Search ............................... 600/372–374; 607/115, 116, 119, 122, 128

(56) References Cited

U.S. PATENT DOCUMENTS

| | | | | |
|---|---|---|---|---|
| 4,608,986 A | | 9/1986 | Beranek et al. ............... 128/786 |
| 5,132,073 A | * | 7/1992 | Nielsen ........................ 264/506 |
| 5,303,704 A | * | 4/1994 | Molacek et al. .............. 128/642 |
| 5,324,321 A | * | 6/1994 | Pohndorf et al. ............. 607/116 |
| 5,324,328 A | * | 6/1994 | Li et al. ....................... 607/129 |
| 5,476,497 A | | 12/1995 | Mower et al. ................ 607/122 |
| 5,584,873 A | | 12/1996 | Shoberg et al. .............. 607/122 |
| 5,935,159 A | | 8/1999 | Cross, Jr. et al. ............ 607/116 |
| 5,957,970 A | | 9/1999 | Shoberg et al. .............. 607/722 |
| 6,438,425 B1 | * | 8/2002 | Miller et al. ................. 607/122 |

* cited by examiner

Primary Examiner—Jeffrey R. Jastrzab
Assistant Examiner—Frances P. Oropeza

(57) ABSTRACT

An implantable endocardial lead intended for use with a cardiac stimulation device includes an elongated lead body of flexible resilient material, for example, silicone rubber or polyurethane, having a longitudinally extending lumen defined by a plurality of longitudinally extending side wall surfaces, adjacent pairs of the side wall surfaces lying in angularly disposed planes and intersecting at an energy absorbing corner ridge. An electrical conductor is located loosely within and extends longitudinally along the lumen between proximal and distal ends. With this construction, forces imposed laterally on the lead body by the conductor engaging the side wall surfaces of the lumen upon bending of the lead body are absorbed without damaging the lead body by reason of engagement of the conductor with a corner ridge causing the corner ridge thereby engaged to recede toward a condition of being coplanar with its subtended pair of side wall surfaces.

15 Claims, 6 Drawing Sheets

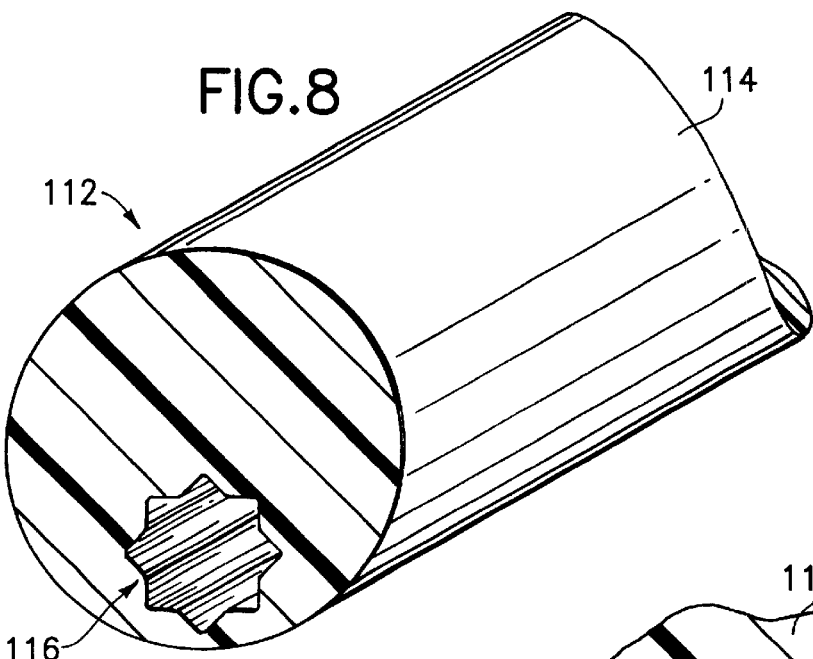
FIG.8
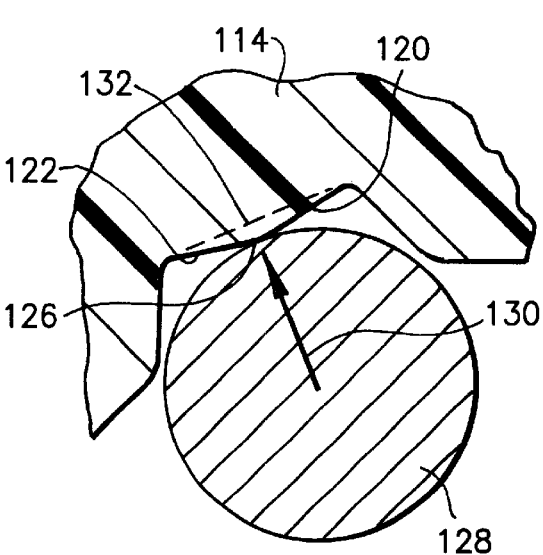
FIG.9
FIG.9A

LEAD CONDUCTOR LUMEN WITH CROSS-SECTIONAL SHAPE TO MINIMIZE EFFECTS OF COMPRESSIVE FORCES

FIELD OF THE INVENTION

The present invention relates generally to an implantable multi-lumen multi-conductor lead for use with an implantable medical device.

BACKGROUND OF THE INVENTION

Permanently implantable electrical lead systems are used in conjunction with implantable medical devices, such as pacemakers and defibrillators. In these applications the lead is used to transmit electrical signals to and/or from the medical device. Leads of this type may be chronically implanted and are expected to exhibit a long service life in a hostile environment of the human body. Cardiac stimulation leads are usually implanted via the cardiovascular venous system such that the distal end of the lead is positioned at an appropriate site within or on top of the surface of the heart.

The traditional lead includes a lead body having a generally circular exterior cross-section and one or more circular lumens, which may be arranged coaxially or parallel to one another. Typically, spiral wound metallic conductors are positioned within one or more lumens of the lead body. The spiral wound conductor also forms a lumen which can receive a stylet to help stiffening the lead as an aid to lead placement during lead implantation.

Alternative conductor designs have been proposed in the context of implantable multiple lumen multiple conductor leads. U.S. Pat. No. 4,608,986 issued to Beranek discloses a round lead having an array of round lumens. This lead places a single "straight" strand of metallic conductor loosely into each lumen. An exotic metal formulation is stated to avoid the problems of breakage due to flexing normally associated with straight conductors.

Current implantable cardiac leads (those cardiac leads implanted for more than 30 days) generally utilize either a type of silicone rubber or a type of polyurethane as the lead's primary insulation material. However, the lead's insulation—especially silicone rubber (though it has good biostability)—is not very strong, has a low tear strength, can abrade very easily, and can cold-flow due to cyclic compressive forces or crushing forces applied to the insulation. Common mechanisms that can result in the insulation thinning and finally breaching to failure, are the effect of cyclic compressive forces or crushing forces on the lead's insulation either from the outside (as in the case of tight sutures on the lead's suture sleeve, forces from the well-known rib/clavicle crush mechanism) or due, simply, to forces from severe bends of the lead body resulting from the implant itself. Another mechanism which can result in the insulation walls thinning because of abrasion or cold flowing occurs when conductors become kinked or bent, so as to impart a compressive force or abrasive action to the inside of the conductor lumen's insulation walls. Such insulation wall thinning due to abrasion and/or cold-flow is especially a concern for leads which are multi-lumen/multi-conductor in design.

Other known designs in which conductors are loosely received in oversized lumina which are sometimes being other than circular in cross section are disclosed, variously, in a number of instances, for example, in U.S. Pat. No. 5,303,704 to Molacek et al.; in U.S. Pat. No. 5,324,321 to Pohndorf et al.; in U.S. Pat. No. 5,476,497 to Mower et al.; and to U.S. Pat. No. 5,957,970 to Shoberg et al.

Also, the invention can be distinguished from the construction found in U.S. Pat. No. 5,584,873 to Shoberg et al., which teaches the use of an empty lumen incremental to the conductor carrying lumen that are used to absorb and/or disperse such compressive or crushing forces.

It was in light of the foregoing that the present invention was conceived and has now been reduced to practice.

SUMMARY OF THE INVENTION

The present invention relates to implantable transvenous or epimyocardial leads intended for use with a cardiac stimulation device. It includes an elongated lead body of flexible resilient material, for example, silicone rubber or polyurethane, having a longitudinally extending lumen defined by a plurality of longitudinally extending side wall surfaces, adjacent pairs of the side wall surfaces lying in angularly disposed planes and intersecting at an energy absorbing corner ridge. An electrical conductor is located loosely within and extends longitudinally along the lumen between proximal and distal ends. With this construction, forces imposed laterally on the lead body by the conductor engaging the side wall surfaces of the lumen upon bending of the lead body are absorbed without damaging the lead body by reason of engagement of the conductor with a corner ridge causing the corner ridge thereby engaged to recede toward a condition of being coplanar with its subtended pair of side wall surfaces.

This invention employs the use of various shapes of conductor lumina within the insulation of the lead to eliminate or minimize the potential for crushing or compressive forces from either outside the lead body or from the conductor or conductors within the lead body. Such a situation can cause an abrasive and/or a cold flow effect on the lead's insulation walls of the lead surrounding each conductor. Conventional round lumen walls are not able to disperse or absorb the compressive and/or abrasive forces that can develop, and the insulation of such a lead can therefore become thinned to the point where ultimate failure of the walls of the insulation can occur. Stated another way, conventional, round conductor carrying lumina cannot prevent or mitigate the compressive or crushing forces from causing the conductor to press against (i.e. cyclic compression) or abrade against the insulation's lumen walls. However, a lumen, which has a shape, that allows for the absorption and/or dispersion of such compressive or crushing forces can reduce, minimize, or even prevent the abrasion or cold flow from occurring to the insulation's lumen walls.

A primary feature of the invention, then, is the provision of an insulation conductor lumen design for use in cardiac leads which allows for the absorption or dispersion of applied forces to the lead and the lead's conductors which, in its absence, can cause the conductors to abrade or cause cold flow to the insulation's lumen walls. Use of the shaped lumen disclosed herein can minimize or even prevent such abrasion and/or cold flow of the insulation.

More specifically, the invention relates to a cardiac bipolar or multi-polar lead in which the primary insulation tubing is silicone rubber, polyurethane or any other suitable material which has at least two or more conductor-carrying-lumen within the lead body, which have a cross-sectional lumen shape that is not round, but is of any shape which can disperse and/or absorb stresses created by external compressive, bending, and/or crushing forces; or stresses created by internal compressive, bending, and/or crushing forces due to the presence of each conductor within the conductor carrying lumen or due to other internal structures and forces.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

FIG. 8 is a perspective view, partially cut away and shown in section, of still another embodiment of implantable cardiac lead according to the invention;

FIG. 9 is a detail cross-section view illustrating an electrical conductor positioned within a lumen in the lead illustrated in FIG. 9;

FIG. 9A is a further detail cross section view of FIG. 9 illustrating the interaction, according to the invention between the electrical conductor and the lumen in the lead;

DETAILED DESCRIPTION OF THE PREFERRED EMBODIMENTS

Figure 1:
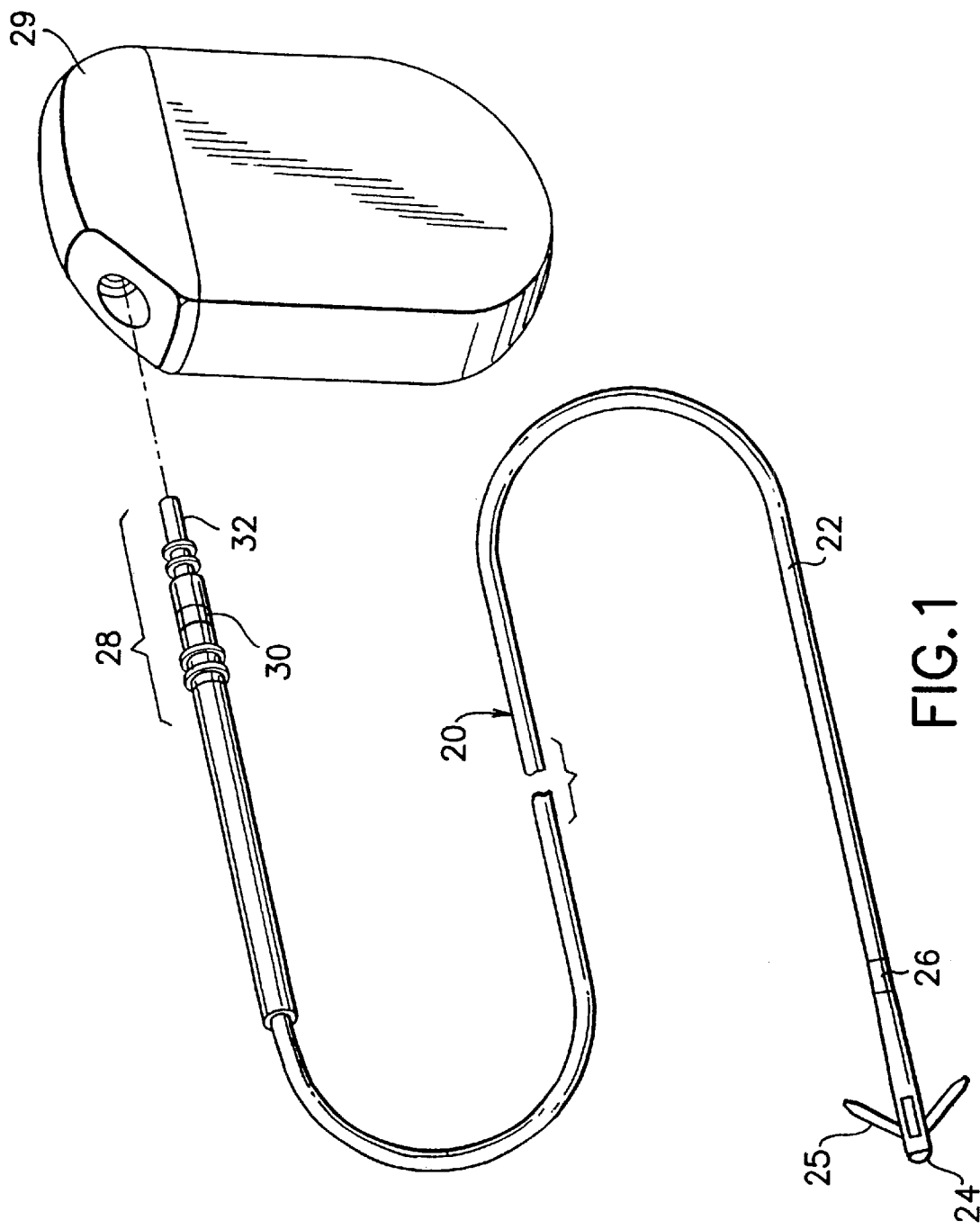
FIG. 1 is a perspective exploded view of a body implantable lead positioned for engagement at one end with heart tissue and at the other end for insertion into a body stimulation device such as a pacemaker and/or defibrillator.

Turn now to the drawings and, initially to FIG. 1, which generally illustrates a body implantable lead 20 of the endocardial type incorporating features of the present invention. Although the present invention will be described with reference to the embodiments shown in the drawings, it should be understood that the present invention can be embodied in many alternate forms or embodiments. In addition, any suitable size, shape or type of elements or materials could be used.

The lead 20, illustrated to be of a bipolar design, includes an insulating sheath 22 interconnecting a distal electrode 24 secured adjacent an interior wall of an organ such as the heart by means, for example, of fixing tines 25, which engage the tissue or trabeculae of the heart and an electrical connector 28 at a proximal end to which can be attached a source of electrical energy such as a pacemaker 29. In a known manner, connector ring terminal 30 of the electrical connector 28 is electrically in common with an anode ring electrode 26 at the distal end of the lead 20, and connector pin terminal 32 is electrically in common with the cathode tip electrode 24 at the distal end of the lead.

Figure 2:
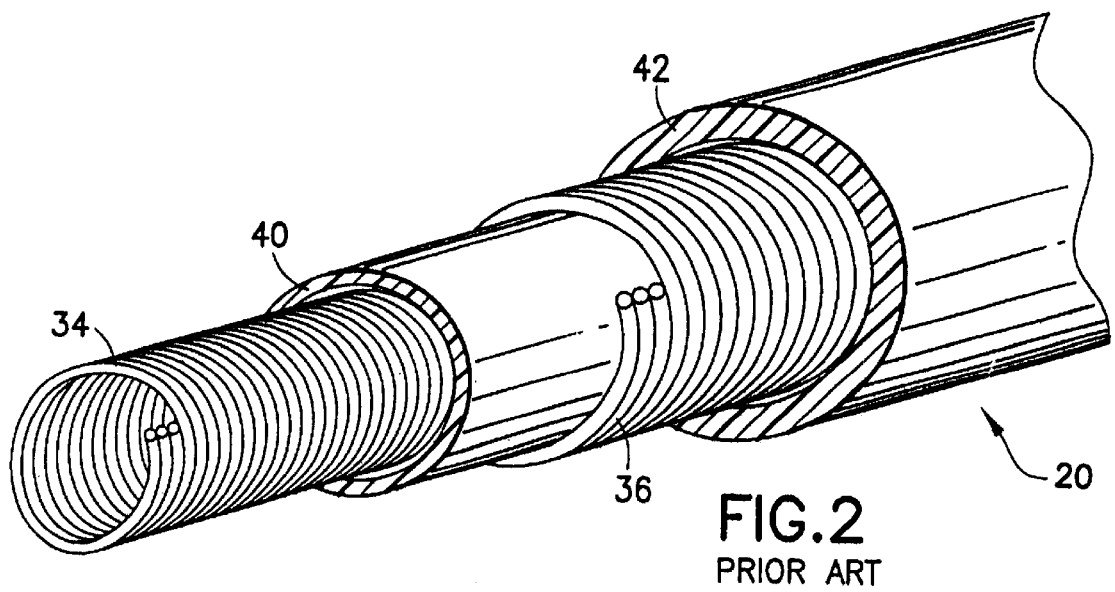
FIG. 2 is a perspective view, partially cut away and shown in section, of one construction of a known implantable cardiac lead.

As earlier explained, but now with reference to FIG. 2, a typical known implantable cardiac lead 20 implanted for more than 30 days generally utilizes either a type of silicone rubber or a type of polyurethane as the lead's primary insulation material. As illustrated, the lead 20 includes an inner conductor coil 34 which extends to the distal electrode 24 (FIG. 1), for example, and an outer conductor coil 36 which extends to the ring electrode 26 (FIG. 1). An inner insulating sheath 40, typically of silicone rubber, insulates the inner conductor coil from the outer conductor coil and an outer insulating sheath 42 which may similarly be of silicone rubber insulates the outer conductor coil 36 from any external grounding agents.

However, while the insulating sheaths 40, 42 for the lead 20 have excellent biostability characteristics, silicone rubber which is a preferred material for this purpose, is not very strong, has a low tear strength, can abrade very easily, and can cold-flow due to cyclic compressive forces or crushing forces applied to the insulation. Common mechanisms that can result in the insulation thinning and finally breaching to failure, are the effect of cyclic compressive forces or crushing forces on the insulating sheaths either from the outside. These deleterious forces may result from tight sutures on the lead's suture sleeve, forces from the well-known rib/clavicle crush mechanism, or may be due simply to forces from severe bends of the lead body resulting from the implant, itself. Another mechanism which can result in the insulation walls thinning because of abrasion or cold flowing occurs when conductors become kinked or bent, so as to impart a compressive force or abrasive action to the inside of the conductor lumen's insulation walls.

Figure 3:
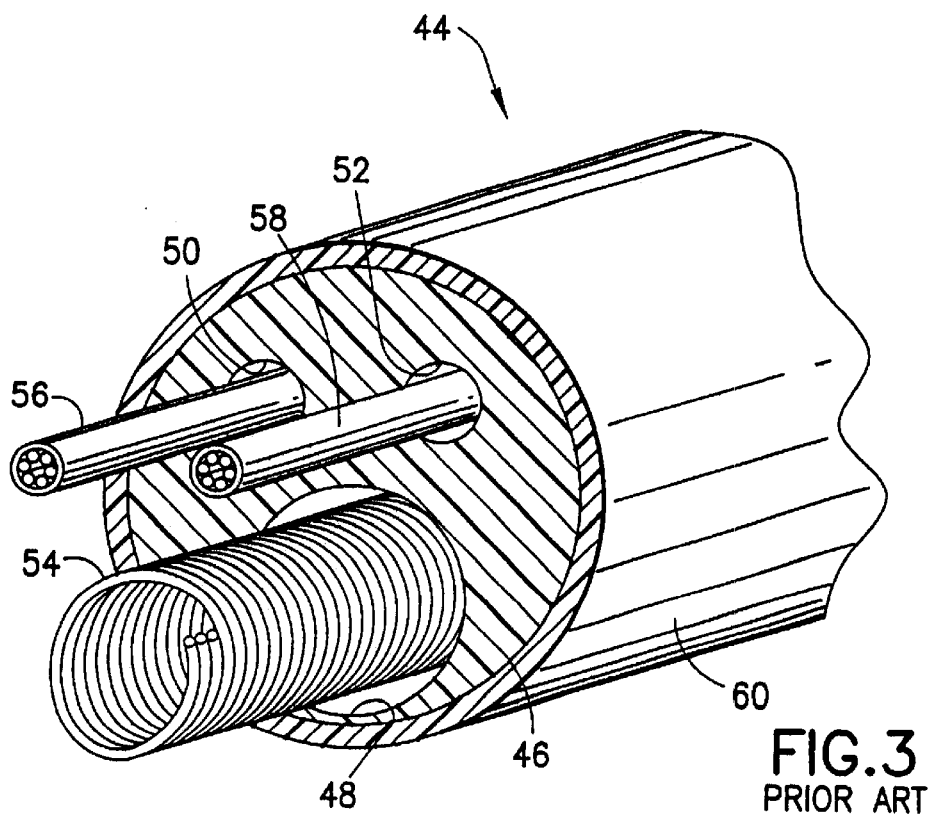
FIG. 3 is a perspective view, partially cut away and shown in section, of another construction of a known implantable cardiac lead.

Such insulation wall thinning due to abrasion and/or cold-flow is especially of concern for leads which are multi-lumen/multi-conductor in design. Another known configuration of this type is illustrated in FIG. 3. In this exemplary instance, a lead 44 includes an insulating sheath 46 with longitudinally extending lumina 48, 50, and 52 of circular cross section. A PTFE-coated conductor coil 54 is received in the lumen 48 for connection to the distal electrode 24 and redundant ETFE (ethylene-tetrafluoroethylene) coated cable conductors 56, 58 are received in the lumina 50, 52, respectively for connection to the ring electrode. Construction of the lead 44 is completed with the application of an outer polyurethane sheath 60 overlying the insulating sheath 46.

As will be explained below, this disclosure presents the use of various shapes of conductor lumina in place of the lumina 48, 50, 52 within the lead's insulation to eliminate or minimize the potential for crushing or compressive forces from either outside the lead body or from within the lead body, due to the conductors in the lead, which can cause an abrasive and/or a cold flow effect on the insulation walls of the lead surrounding the conductors. Conventional, round lumen walls are not able to disperse or absorb the compressive/abrasive forces that can develop, and such insulation of the lead can therefore become thinned to the point where ultimate failure of the insulation's walls can occur. Stated another way, conventional, round conductor carrying lumina cannot prevent or mitigate the compressive or crushing forces from causing the conductor to press against (i.e. cyclic compression) or abrade against the insulation's lumen walls. However, lumina which have a shape that allows for the absorption and/or dispersion of such compressive or crushing forces can reduce, minimize, or even prevent the abrasion or cold flow from occurring to the insulation's lumen walls.

Figure 4:
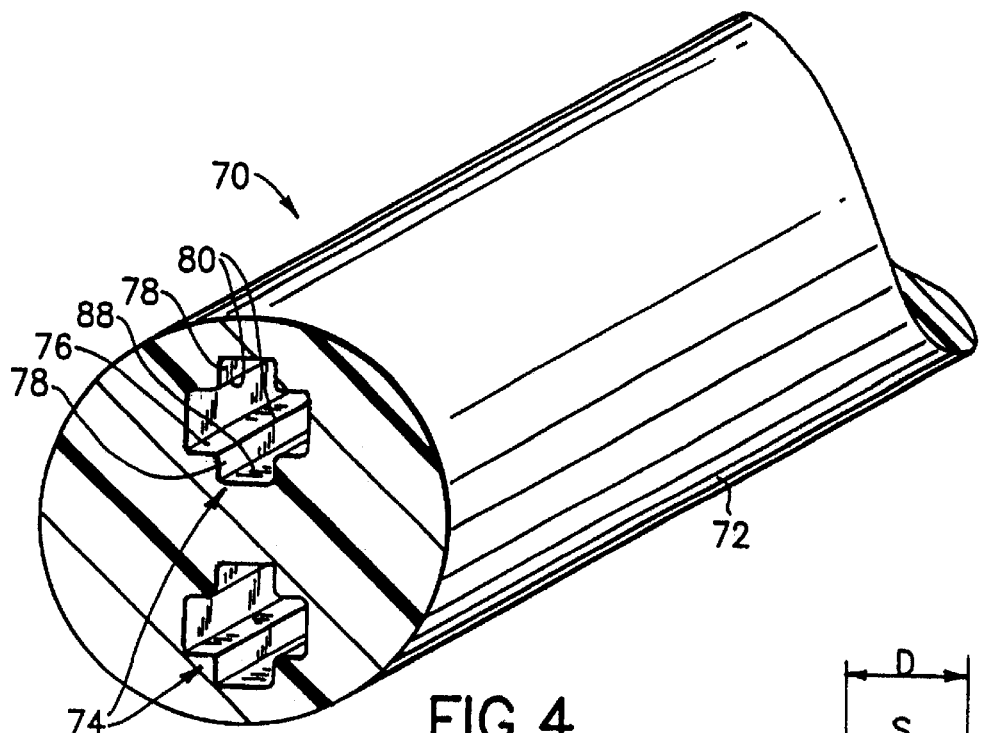
FIG. 4 is a perspective view, partially cut away and shown in section, of an implantable cardiac lead embodying the invention.
Figure 5:
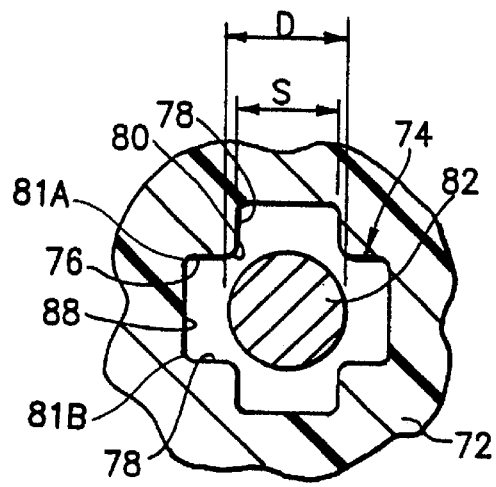
FIG. 5 is a detail cross-section view illustrating an electrical conductor positioned within a lumen in the lead illustrated in FIG. 4.
Figure 5A:
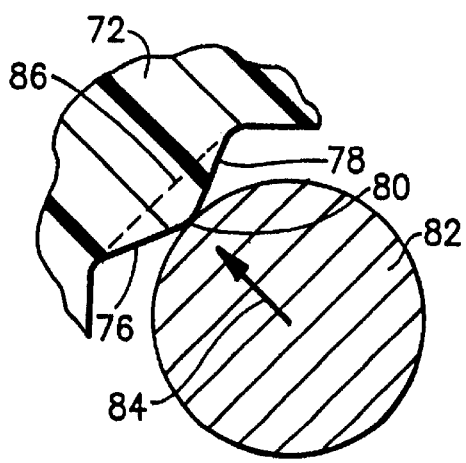
FIG. 5A is a further detail cross-section view of FIG. 5 illustrating the interaction, according to the invention, between the electrical conductor and the lumen in the lead.

Turn now to FIGS. 4, 5, and 5A for one embodiment of the invention. In this instance, an implantable endocardial lead 70 includes an elongated lead body 72 of flexible resilient material such as silicone rubber, polyurethane, or a composite of silicone rubber and polyurethane. The lead 70 has at least one longitudinally extending lumen 74 defined by a plurality of longitudinally extending side wall surfaces 76, 78, adjacent pairs of the side wall surfaces lying in angularly disposed planes and intersecting at an energy absorbing corner ridge 80. Actually, the lead body 72 may have two or more lumina 74, two being illustrated in FIG. 4. An electrical conductor 82 (see FIGS. 5 and 5A) is located loosely within each lumen 74 and extends longitudinally along the lumen between proximal and distal ends. For proper operation of the invention, the diameter D or minimum cross-section (if other than of circular cross-section) of the electrical conductor 82 is greater than the spacing S between adjacent corner ridges 80. Preferably, the energy absorbing corner ridges 80 are rounded to minimize stress concentrations on the electrical conductor and to maximize surface area for engagement between the electrical conductor and the lead body along each corner ridge 80.

With this construction, forces imposed laterally on the lead body 72 by the electrical conductor 82 engaging the side wall surfaces 76, 78 of the lumen 74 upon bending of the lead body 72 are absorbed without damaging the lead body by reason of engagement of the conductor with a corner ridge 80. Viewing especially FIG. 5A, this operation causes the corner ridge 80 thereby engaged to recede in the direction of an arrow 84 and approach a condition of being coplanar with its subtended pair of side wall surfaces 76, 78. A fully coplanar condition is indicated by a dashed line 86 in FIG. 5A.

More specifically, in this instance, the lumen 74 has a transverse cross sectional shape in the form of a cross having adjacent legs defined by opposed side wall surfaces 76, 78 and end wall surfaces 88 connecting the side wall surfaces. Again, as earlier described, the side wall surfaces 76, 78 of adjacent legs intersect at the energy absorbing rounded corner ridges 80. In similar fashion, the side wall surfaces 76, 78 mutually intersect, respectively, with the end wall surfaces 88 at corner creases 81A, 81B which, similar to the corner ridges 80, are rounded to minimize stress concentrations on the electrical conductor 82 and to maximize surface area for engagement between the electrical conductor and the lead body 72 along the length of each corner crease 81A, 81B.

Figure 6:
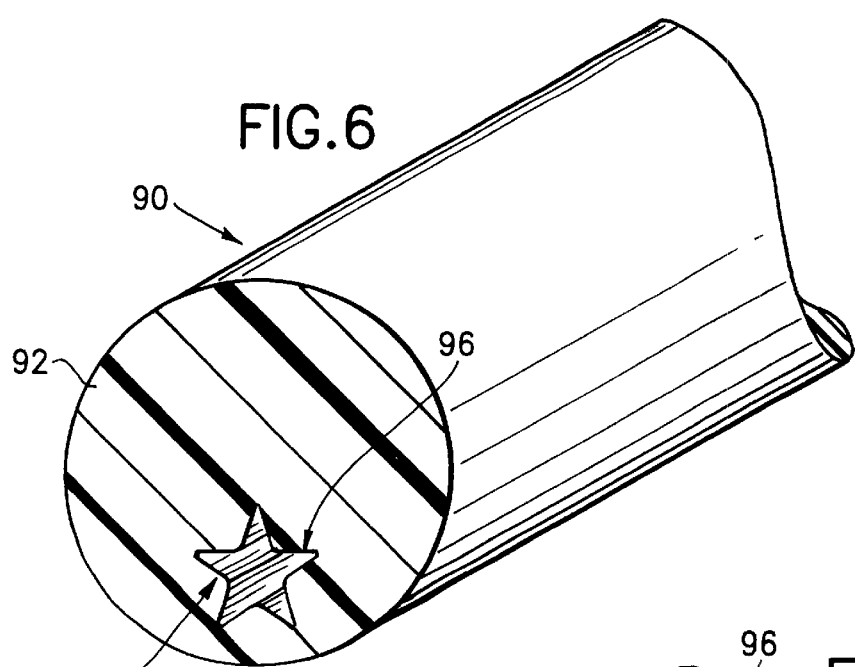
FIG. 6 is a perspective view, partially cut away and shown in section, of another embodiment of implantable cardiac lead according to the invention.
Figure 7:
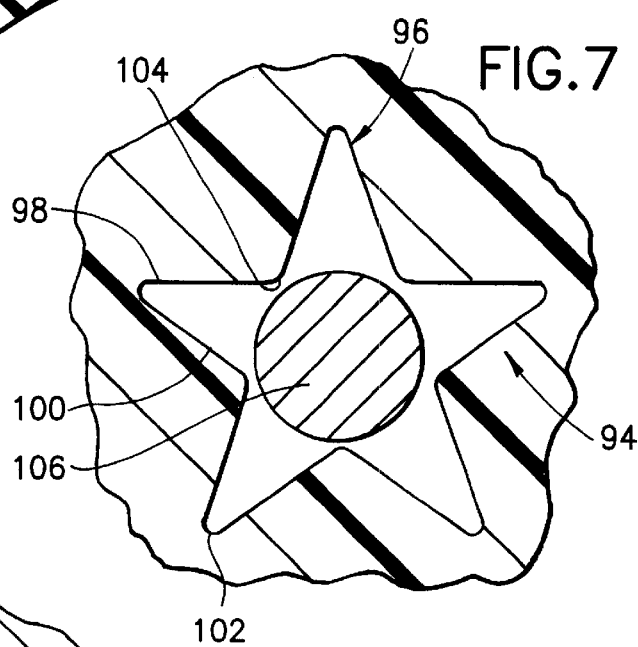
FIG. 7 is a detail cross-section view illustrating an electrical conductor positioned within a lumen in the lead illustrated in FIG. 6.
Figure 7A:
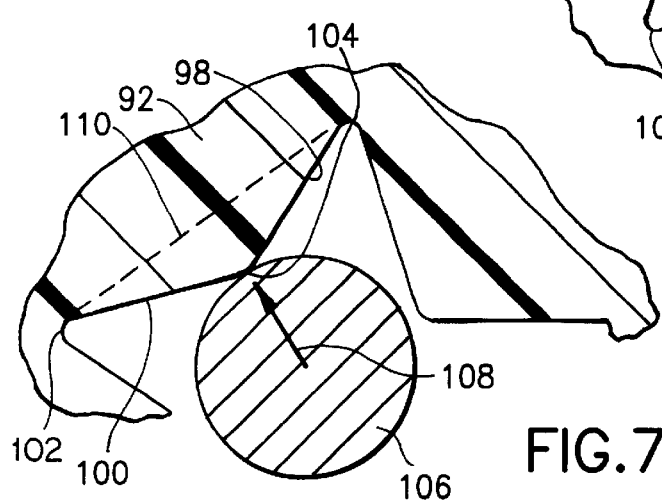
FIG. 7A is a further detail cross-section view of FIG. 7 illustrating the interaction, according to the invention, between the electrical conductor and the lumen in the lead.

Turn now to FIGS. 6, 7, and 7A for another embodiment of the invention. In this instance, an implantable endocardial lead 90 includes an elongated lead body 92 of flexible resilient material generally as earlier described. Again, the lead 90 has at least one longitudinally extending lumen 94 but in this instance, the lumen has a transverse cross sectional shape in the form of a star having a plurality of outwardly extending legs 96 at discrete peripheral locations. Each leg 96 is defined by opposed side wall surfaces 98, 100 intersecting at corner creases 102 rounded in the manner of the corner creases 81A and 81B. At the same time, the side wall surfaces of adjacent legs intersect at energy absorbing, and rounded, corner ridges 104. An electrical conductor 106 (see FIGS. 7 and 7A) is located loosely within each lumen 94 and extends longitudinally along the lumen between proximal and distal ends. As in the instance of the embodiment illustrated in FIGS. 4, 5, and 5A, for proper operation of the invention, the diameter of the electrical conductor 106 is greater than the spacing between adjacent corner ridges 104. Also, it is preferable that the absorbing corner ridges 104 are rounded for the reasons mentioned earlier.

With this construction, forces imposed laterally on the lead body 92 by the electrical conductor 106 engaging the side wall surfaces 98, 100 of the lumen 94 upon bending of the lead body 92 are absorbed without damaging the lead body by reason of engagement of the conductor with a corner ridge 104. Viewing especially FIG. 7A, this operation causes the corner ridge 104 thereby engaged to recede in the direction of an arrow 108 and approach a condition of being coplanar with its subtended pair of side wall surfaces 98, 100. A fully coplanar condition is indicated by a dashed line 110 in FIG. 7A.

Turn now to FIGS. 8, 9, and 9A for still another embodiment of the invention. In this instance, an implantable endocardial lead 112 includes an elongated lead body 114 of flexible resilient material generally as earlier described. Again, the lead 112 has at least one longitudinally extending lumen 116 but in this instance, the lumen has a transverse cross sectional shape in the form of a modified star having a plurality of outwardly extending legs 118 at discrete peripheral locations. Each leg 118 is defined by opposed side wall surfaces 120, 122 intersecting at corner creases 124, rounded in a manner similar to the corner creases 81A, 81B, and 102, the side wall surfaces of adjacent legs intersecting at energy absorbing corner ridges 126, rounded in the manner of corner ridges 80 and 104. An electrical conductor 128 (see FIGS. 9 and 9A) is located loosely within each lumen 116 and extends longitudinally along the lumen between proximal and distal ends. As in the instance of the earlier illustrated embodiments, for proper operation of the invention, the diameter of the electrical conductor 128 is greater than the spacing between adjacent corner ridges 126. Also, it is preferable that the absorbing corner ridges 126 are rounded for the reasons mentioned earlier.

With this construction, as with the earlier described embodiments, forces imposed laterally on the lead body 114 by the electrical conductor 128 engaging the side wall surfaces 120, 122 of the lumen 116 upon bending of the lead body 114 are absorbed without damaging the lead body by reason of engagement of the conductor with a corner ridge 126. Viewing especially FIG. 9A, this operation causes the corner ridge 126 thereby engaged to recede in the direction of an arrow 130 and approach a condition of being coplanar with its subtended pair of side wall surfaces 120, 122. A fully coplanar condition is indicated by a dashed line 132 in FIG. 9A.

Figure 10:
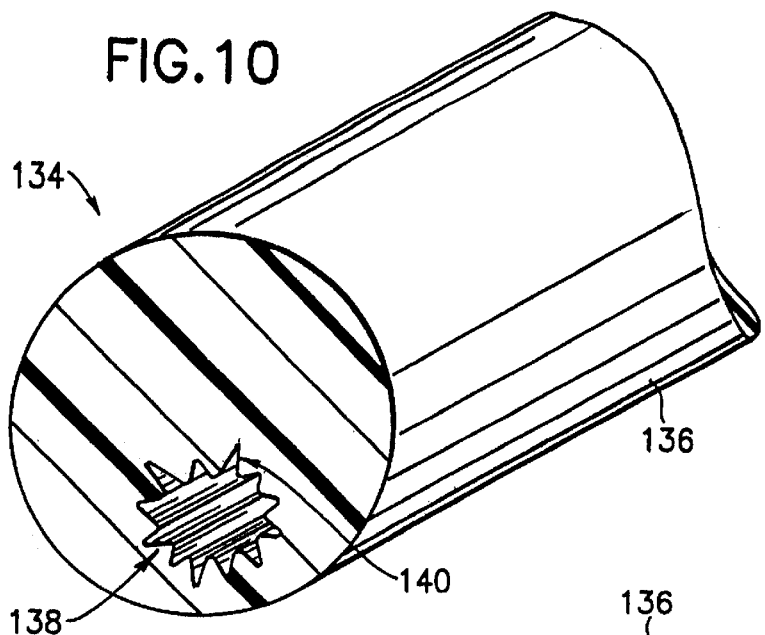
FIG. 10 is a perspective view, partially cut away and shown in section, of an yet another implantable cardiac lead embodying the invention.
Figure 11:
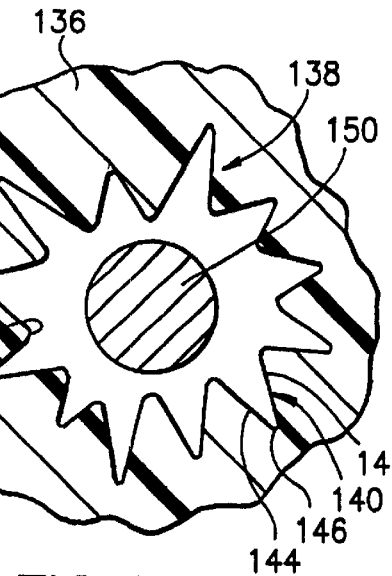
FIG. 11 is a detail cross-section view illustrating an electrical conductor positioned within a lumen in the lead illustrated in FIG. 10.
Figure 11A:
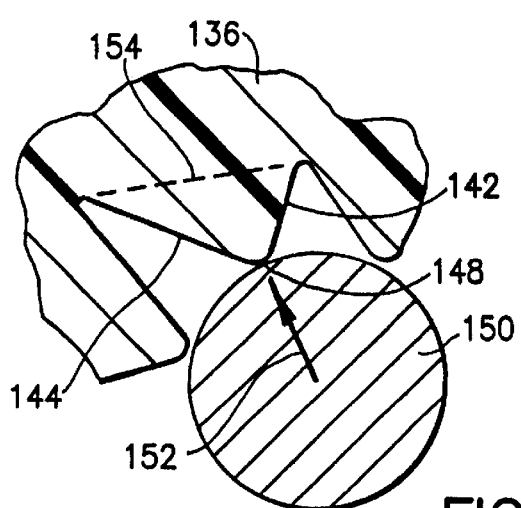
FIG. 11A is a further detail cross-section view of FIG. 11 illustrating the interaction, according to the invention between the electrical conductor and the lumen in the lead.

Turn now to FIGS. 10, 11, and 11A for yet another embodiment of the invention. In this instance, an implantable endocardial lead 134 includes an elongated lead body 136 of flexible resilient material generally as earlier described. Again, the lead 134 has at least one longitudinally extending lumen 138 but in this instance, the lumen has an irregular transverse cross sectional shape having a plurality of outwardly extending legs 140 at discrete peripheral locations. Each leg 140 is defined by opposed side wall surfaces 142, 144 intersecting at rounded corner creases 146, the side wall surfaces of adjacent legs intersecting at rounded energy absorbing corner ridges 148. An electrical conductor 150 (see FIGS. 11 and 11A) is located loosely within each lumen 138 and extends longitudinally along the lumen between proximal and distal ends. As in the instance of the earlier illustrated embodiments, for proper operation of the invention, the diameter of the electrical conductor 150 is greater than the spacing between adjacent corner ridges 148. Also, it is preferable that the absorbing corner ridges 148 are rounded for the reasons mentioned earlier. with this construction, as with each of the earlier described embodiments, forces imposed laterally on the lead body 136 by the electrical conductor 150 engaging the side wall surfaces 142, 144 of the lumen 138 upon bending of the lead body 136 are absorbed without damaging the lead body by reason of engagement of the conductor with a corner ridge 148. Viewing especially FIG. 11A, this operation causes the corner ridge 148 thereby engaged to recede in the direction of an arrow 152 and approach a condition of being coplanar with its subtended pair of side wall surfaces 142, 144. A fully coplanar condition is indicated by a dashed line 154 in FIG. 11A.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An implantable endocardial lead extending between proximal and distal ends for use with a cardiac stimulation device comprising:

an elongated lead body of flexible resilient material having a longitudinally extending lumen defined by a plurality of longitudinally extending side wall surfaces, adjacent pairs of the side wall surfaces lying in angularly disposed planes and intersecting at an energy absorbing corner ridge; and an electrical conductor located loosely within and extending longitudinally along the lumen between proximal and distal ends, the diameter of the conductor being greater than the spacing between adjacent corner ridges;

whereby forces imposed laterally on the lead body by the conductor engaging the side wall surfaces of the lumen upon bending of the lead body are absorbed without damaging the lead body by reason of engagement of the conductor with a corner ridge causing the corner ridge thereby engaged to recede toward a condition of being coplanar with its subtended pair of side wall surfaces.

2. An implantable endocardial lead as set forth in claim 1, wherein the energy absorbing corner ridges are rounded.

3. An implantable endocardial lead as set forth in claim 1 including:

an electrical connector being coupled to the proximal end of the electrical conductor.

4. An implantable endocardial lead as set forth in claim 1:

wherein the lead body has a plurality of the longitudinally extending lumina; and wherein an electrical conductor is located loosely within each lumen and extends longitudinally along its associated lumen between proximal and distal ends.

5. An implantable endocardial lead as set forth in claim 1:

wherein the lumen has a transverse cross sectional shape in the form of a cross having adjacent legs defined by opposed side wall surfaces and end wall surfaces connecting the side wall surfaces, the side wall surfaces of adjacent legs intersecting at the energy absorbing corner ridges.

6. An implantable endocardial lead as set forth in claim 5:

wherein the side wall and end wall surfaces mutually intersect at corner creases; and wherein the energy absorbing corner ridges and the corner creases are rounded.

7. An implantable endocardial lead as set forth in claim 1:

wherein the lumen has a transverse cross sectional shape in the form of a star having a plurality of outwardly extending legs at discrete peripheral locations, each leg defined by opposed side wall surfaces intersecting at corner creases, the side wall surfaces of adjacent legs intersecting at energy absorbing corner ridges.

8. An implantable endocardial lead as set forth in claim 7:

wherein the corner creases and energy absorbing corner ridges are rounded.

9. An implantable endocardial lead as set forth in claim 1:

wherein the lumen has an irregular transverse cross sectional shape with a plurality of outwardly extending legs at discrete peripheral locations, each leg defined by opposed side wall surfaces intersecting at a corner crease, the side wall surfaces of adjacent legs intersecting at energy absorbing corner ridges.

10. An implantable endocardial lead as set forth in claim 9, wherein the corner creases and energy absorbing corner ridges are rounded.

11. An implantable endocardial lead as set forth in claim 1, wherein the lead body is composed of silicone rubber.

12. An implantable endocardial lead as set forth in claim 1, wherein the lead body is composed of polyurethane.

13. An implantable endocardial lead as set forth in claim 1, wherein the lead body is composed of a chemical composite of silicone rubber and polyurethane.

14. An implantable endocardial lead as set forth in claim 1, wherein the lead body is composed of a flexible polymeric insulating material.

15. An implantable endocardial lead extending between proximal and distal ends for use with a cardiac stimulation device comprising:

an elongated lead body of flexible resilient material having a longitudinally extending lumen defined by a plurality of longitudinally extending side wall surfaces, adjacent pairs of the side wall surfaces lying in angularly disposed planes and intersecting at an energy absorbing corner ridge; and at least two electrical conductors located loosely within and extending longitudinally along the lumen between proximal and distal ends, the diameter of each of the conductors being greater than the spacing between adjacent corner ridges;

whereby forces imposed laterally on the lead body by the conductors engaging the side wall surfaces of the lumen upon bending of the lead body are absorbed without damaging the lead body by reason of engagement of the conductors with a corner ridge thereby causing the corner ridge thereby engaged to recede toward a condition of being coplanar with its subtended pair of side wall surfaces.

* * * * *